(12) United States Patent
Liu

(10) Patent No.: US 9,345,269 B2
(45) Date of Patent: May 24, 2016

(54) ELECTRONIC CIGARETTE

(71) Applicant: Tuanfang Liu, Ji'an (CN)

(72) Inventor: Tuanfang Liu, Ji'an (CN)

( * ) Notice: Subject to any disclaimer, the term of this patent is extended or adjusted under 35 U.S.C. 154(b) by 417 days.

(21) Appl. No.: 14/098,513

(22) Filed: Dec. 5, 2013

(65) Prior Publication Data

US 2015/0136157 A1 May 21, 2015

(30) Foreign Application Priority Data

Nov. 19, 2013 (CN) .................... 2013 2 0730610 U

(51) Int. Cl.
*A24F 47/00* (2006.01)
*A61M 15/06* (2006.01)

(52) U.S. Cl.
CPC .............. *A24F 47/008* (2013.01); *A61M 15/06* (2013.01)

(58) Field of Classification Search
CPC ...... A61M 15/06; A24F 47/00; A24F 47/002; A24F 47/004; A24F 47/008
See application file for complete search history.

(56) References Cited

U.S. PATENT DOCUMENTS

| | | | | |
|---|---|---|---|---|
| 2014/0190501 A1* | 7/2014 | Liu | ........................ | A24F 47/008 131/329 |
| 2014/0202472 A1* | 7/2014 | Levitz | ..................... | A24F 13/22 131/187 |
| 2014/0318557 A1* | 10/2014 | Bremer | ..................... | A24F 1/00 131/328 |
| 2015/0090256 A1* | 4/2015 | Chung | ................ | A61M 15/002 128/202.21 |
| 2015/0173422 A1* | 6/2015 | Liu | ........................ | A24F 47/008 131/329 |
| 2015/0216234 A1* | 8/2015 | Chung | .................. | A24F 47/008 131/329 |
| 2016/0000145 A1* | 1/2016 | Liu | ........................ | A24F 47/002 131/329 |

* cited by examiner

*Primary Examiner* — Anthony Calandra
(74) *Attorney, Agent, or Firm* — Matthias Scholl, PC; Matthias Scholl

(57) ABSTRACT

An electronic cigarette, including a cigarette holder assembly, an atomization assembly, a glass container for accommodating smoke oil, and a gas flow regulator. The cigarette holder assembly includes a mouthpiece, a first sealing ring, a seat for supporting the mouthpiece, a fixed screw, and a pole. The atomization assembly includes a pair of heating wires, a glass casing, a second sealing ring, a third sealing ring, oil-guiding cotton, a limit cover, an insulating ring, and a fixed ring. The glass container includes a first sealing gasket and a second sealing gasket which are respectively disposed at both ends of the glass container. The gas flow regulator includes a control ring, a steel ball, a spring, and a rotary button. The first sealing ring of the cigarette holder assembly is sleeved on the mouthpiece, and the mouthpiece is fixed on the seat via the fixed screw.

3 Claims, 2 Drawing Sheets

ELECTRONIC CIGARETTE

CROSS-REFERENCE TO RELATED APPLICATIONS

Pursuant to 35 U.S.C. §119 and the Paris Convention Treaty, this application claims the benefit of Chinese Patent Application No. 201320730610.8 filed Nov. 19, 2013, the contents of which, are incorporated herein by reference. Inquiries from the public to applicants or assignees concerning this document or the related applications should be directed to: Matthias Scholl P.C., Attn.: Dr. Matthias Scholl Esq., 14781 Memorial Drive, Suite 1319, Houston, Tex. 77079.

BACKGROUND OF THE INVENTION

1. Field of the Invention

The invention relates to an electronic cigarette.

2. Description of the Related Art

It is well-known that smoking is harmful to health, but there are still hundreds of millions of smokers in the world, and the trend is continuing. To purify the environment, prohibition of smoking in public places has become the consensus. Thus, cigarette substitutes, such as patches for quitting smoking, nicotine mouthwash, nicotine gum, nicotine drink, flourish in the market. Although the cigarette substitutes are a step in the right direction as they do not deliver tar, nicotine is only slowly absorbed in the blood and thus the achieved effective peak concentration of nicotine is relatively low, and the feeling of satisfaction resulting from a high concentration of tobacco alkali is not achieved. Meanwhile, users consuming cigarette substitutes are deprived of smoking actions such as inhaling, exhaling, and puffing.

SUMMARY OF THE INVENTION

In view of the above-described problems, it is one objective of the invention to provide an electronic cigarette that is convenient for use and causes no pollution. When using the electronic cigarette, an enjoyable experience resulting from the smoking actions such as inhaling, exhaling, and puffing can be achieved, and the gas flow of the inhaling and exhaling is adjustable.

To achieve the above objective, in accordance with one embodiment of the invention, there is provided an electronic cigarette, comprising a cigarette holder assembly, an atomization assembly, a glass container for accommodating smoke oil, and a gas flow regulator. The cigarette holder assembly comprises a mouthpiece, a first sealing ring, a seat for supporting the mouthpiece, a fixed screw, and a pole. The atomization assembly comprises a pair of heating wires, a glass casing, a second sealing ring, a third sealing ring, oil-guiding cotton, a limit cover, an insulating ring, and a fixed ring. The glass container comprises a first sealing gasket and a second sealing gasket which are respectively disposed at both ends of the glass container. The gas flow regulator comprises a control ring, a steel ball, a spring, and a rotary button.

The first sealing ring of the cigarette holder assembly is sleeved on the mouthpiece, and the mouthpiece is fixed on the seat via the fixed screw. The first sealing gasket is fixed between the seat and the fixed screw. The pole is disposed at a lower part of the mouthpiece and fixed by a screw. The second sealing ring is disposed at one end of the pole for sealing the heating wires. The glass container for accommodating smoke oil is disposed at a lower part of the cigarette holder assembly. The heating wires are inserted in the glass casing and fixed by the limit cover and the fixed ring. The oil-guiding cotton is disposed in the glass casing, and the insulating ring is connected to the fixed ring; the gas flow regulator is disposed at a lower part of the atomization assembly.

In a class of this embodiment, the mouthpiece is made of metal material.

In a class of this embodiment, the atomization assembly comprises a threaded copper ring and a joint.

Advantages of the invention are summarized as follows:

1) two heating wires are employed, the smoke concentration is dense, the taste is pure, and no oil leaks;
2) the heating wires are disposed at the bottom of the electronic cigarette, the heating wires and other auxiliaries such as fiber strands are hidden in the electronic cigarette, which presents a beautiful external appearance;
3) the pole transports the gas flow, separates the smoke oil from the air, and connects the cigarette holder assembly to the atomization assembly;
4) the gas flow regulator comprises the rotary button which is capable of controlling the gas flow; and
5) the glass container is fixed by screws whereby strengthening the connection of the cigarette holder assembly and the atomization assembly.

BRIEF DESCRIPTION OF THE DRAWINGS

The invention is described hereinbelow with reference to accompanying drawings, in which.

DETAILED DESCRIPTION OF THE EMBODIMENTS

Figure 1:
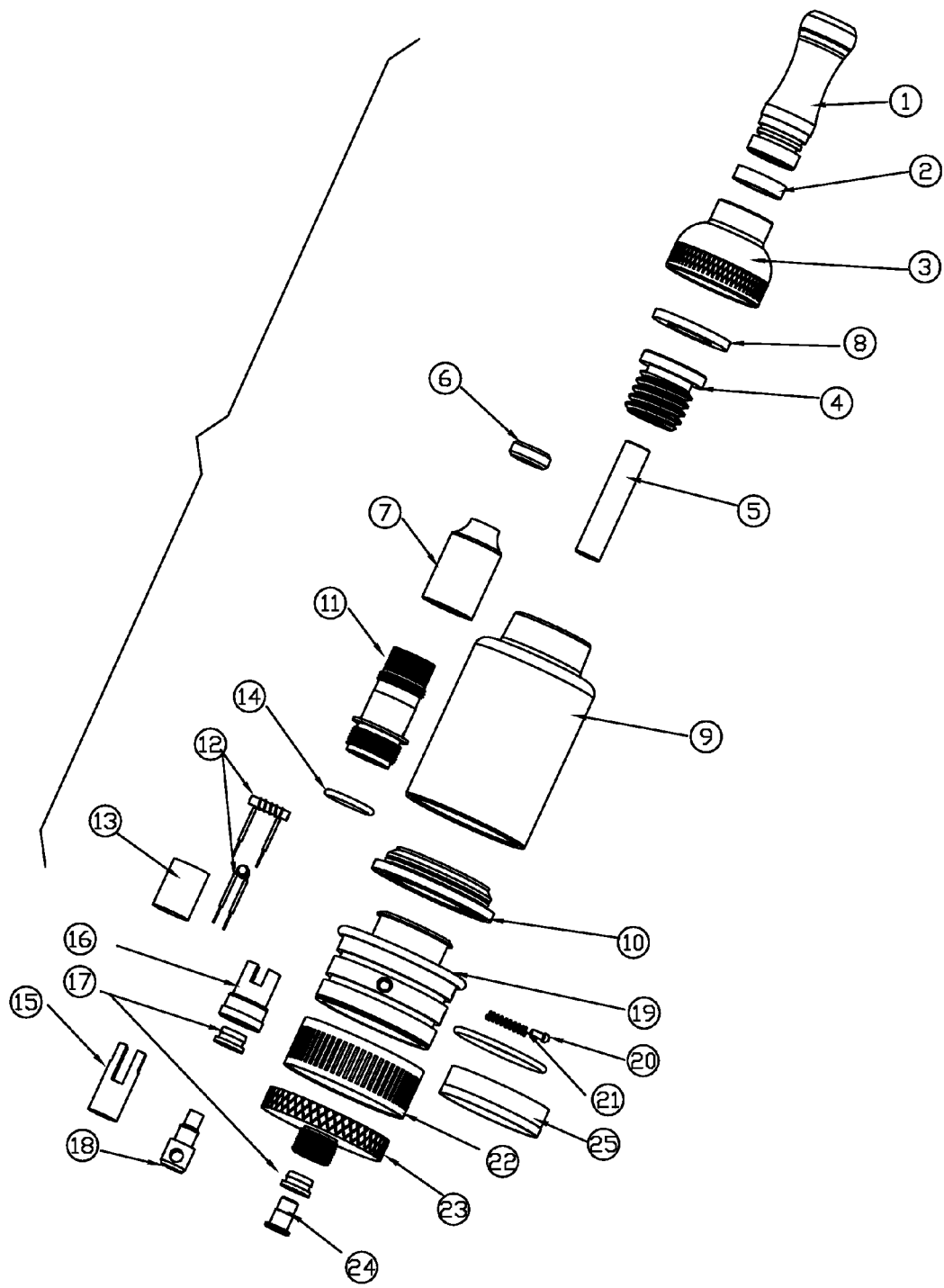
FIG. 1 is an exploded view of an electronic cigarette of the invention.
Figure 2:
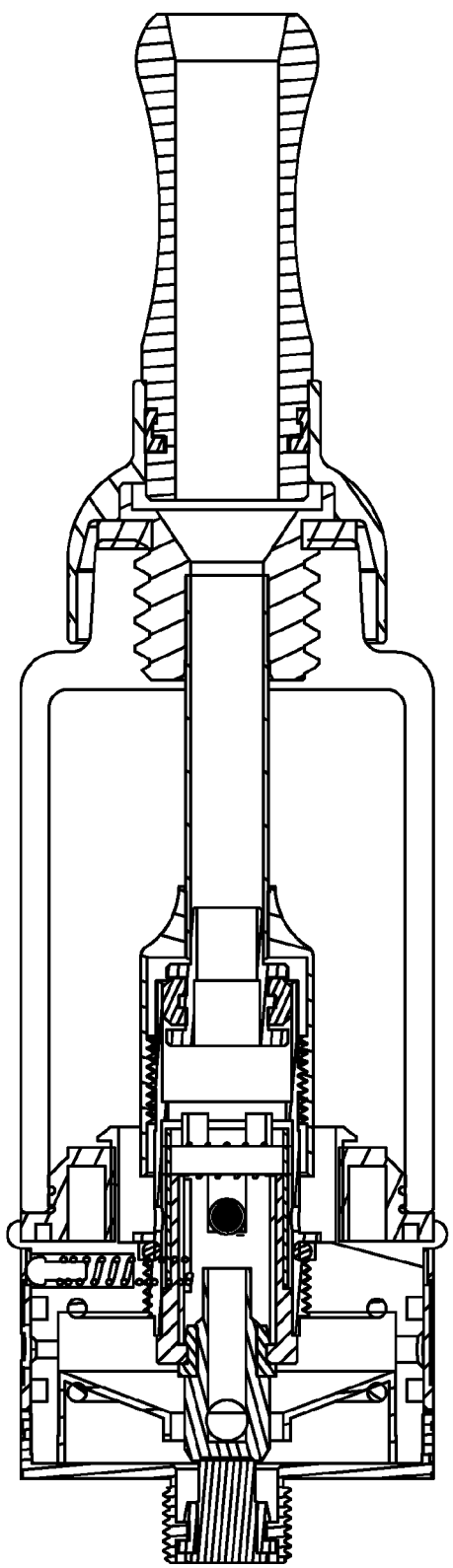
FIG. 2 is a schematic diagram of an electronic cigarette of the invention.

As shown in FIGS. 1 and 2, an electronic cigarette comprises a cigarette holder assembly, an atomization assembly, a glass container 9 for accommodating smoke oil, and a gas flow regulator. The cigarette holder assembly comprising a mouthpiece 1, a first sealing ring 2, a seat 3 for supporting the mouthpiece, a fixed screw 4, and a pole 5. The atomization assembly comprising a pair of heating wires 12, a glass casing 15, a second sealing ring 6, a third sealing ring 14, oil-guiding cotton 13, a limit cover 11, an insulating ring 17, and a fixed ring 16. The glass container comprising a first sealing gasket 8 and a second sealing gasket 10 which are respectively disposed at both ends of the glass container. The gas flow regulator comprising a control ring 19, a steel ball 20, a spring 21, and a rotary button 22.

The first sealing ring of the cigarette holder assembly is sleeved on the mouthpiece, and the mouthpiece is fixed on the seat via the fixed screw. The first sealing gasket is fixed between the seat and the fixed screw. The pole is disposed at a lower part of the mouthpiece and fixed by a screw 7. The second sealing ring is disposed at one end of the pole for sealing the heating wires. The glass container for accommodating smoke oil is disposed at a lower part of the cigarette holder assembly. The heating wires are inserted in the glass casing and fixed by the limit cover and the fixed ring. The oil-guiding cotton is disposed in the glass casing, and the insulating ring is connected to the fixed ring. The gas flow regulator is disposed at a lower part of the atomization assembly for controlling the gas flow.

Preferably, the mouthpiece is made of metal material.

Furthermore, the atomization assembly comprises a joint 18. The rotary button 22 is disposed at the bottom of the glass casing 15. A cover 25 for receiving leaked oil, a threaded copper ring 23, and an insulating joint 24 are disposed at the lower part of the glass casing 15.

The electronic cigarette is assembled according to the following steps:

1. The atomization assembly and the gas flow regulator disposed at the bottom of the heating wires are fixed by screws and sealing gaskets.
2. The cigarette holder assembly and the glass container are fixed by screws.
3. The glass container is filled with smoke oil to a desired scale mark.
4. The heating wires are assembled and fixed on the atomization assembly, and the atomization assembly is connected to the cigarette holder assembly.
5. The mouthpiece of the cigarette holder assembly is inserted into the seat and fixed on the glass container.
6. The heating wires are connected to power supply for use.

While particular embodiments of the invention have been shown and described, it will be obvious to those skilled in the art that changes and modifications may be made without departing from the invention in its broader aspects, and therefore, the aim in the appended claims is to cover all such changes and modifications as fall within the true spirit and scope of the invention.

The invention claimed is:

1. An electronic cigarette, comprising:
   a) a cigarette holder assembly, the cigarette holder assembly comprising a mouthpiece, a first sealing ring, a seat for supporting the mouthpiece, a fixed screw, and a pole;
   b) an atomization assembly, the atomization assembly comprising a pair of heating wires, a glass casing, a second sealing ring, a third sealing ring, oil-guiding cotton, a limit cover, an insulating ring, and a fixed ring;
   c) a glass container for accommodating smoke oil, the glass container comprising a first sealing gasket and a second sealing gasket which are respectively disposed at both ends of the glass container; and
   d) a gas flow regulator, the gas flow regulator comprising a control ring, a steel ball, a spring, and a rotary button;
   wherein
      the first sealing ring of the cigarette holder assembly is sleeved on the mouthpiece, and the mouthpiece is fixed on the seat via the fixed screw;
      the first sealing gasket is fixed between the seat and the fixed screw;
      the pole is disposed at a lower part of the mouthpiece and fixed by a screw;
      the second sealing ring is disposed at one end of the pole for sealing the heating wires;
      the glass container for accommodating smoke oil is disposed at a lower part of the cigarette holder assembly;
      the heating wires are inserted in the glass casing and fixed by the limit cover and the fixed ring;
      the oil-guiding cotton is disposed in the glass casing, and the insulating ring is connected to the fixed ring; and
      the gas flow regulator is disposed at a lower part of the atomization assembly.

2. The electronic cigarette of claim 1, wherein the mouthpiece is metal.

3. The electronic cigarette of claim 1, wherein the atomization assembly comprises a threaded copper ring and a joint.

* * * * *